United States Patent [19]

Jones et al.

[11] Patent Number: 5,410,074
[45] Date of Patent: * Apr. 25, 1995

[54] PROCESS FOR PREPARING SULFONIUM OR SULFOXONIUM SALTS OF N-PHOSPHONOMETHYLGLYCINE

[75] Inventors: Raymond V. H. Jones, West Lothian; Elizabeth S. C. Simpson, Lanarkshire, both of Scotland

[73] Assignee: Imperial Chemical Industries PLC, London, Great Britain

[*] Notice: The portion of the term of this patent subsequent to Apr. 5, 2011 has been disclaimed.

[21] Appl. No.: 131,044

[22] Filed: Dec. 10, 1993

Related U.S. Application Data

[62] Division of Ser. No. 883,087, May 15, 1992, Pat. No. 5,300,680.

Foreign Application Priority Data

Jun. 4, 1991 [GB] United Kingdom ............... 9111974

[51] Int. Cl.$^6$ .................... C07F 9/28; C07F 9/38
[52] U.S. Cl. ....................................... 562/17
[58] Field of Search ................................ 562/17

[56] References Cited

U.S. PATENT DOCUMENTS

| | | | |
|---|---|---|---|
| 4,315,765 | 2/1982 | Large | 71/87 |
| 4,431,594 | 2/1984 | Broadhurst et al. | 260/502.5 F |
| 4,542,023 | 9/1985 | Lacroix et al. | 514/126 |
| 5,300,680 | 4/1994 | Jones et al. | 562/17 |

FOREIGN PATENT DOCUMENTS 0115466  8/1984  European Pat. Off.
0369076  5/1990  European Pat. Off.

Primary Examiner—Jose G. Dees
Assistant Examiner—Barbara S. Frazier
Attorney, Agent, or Firm—Marian T. Thomson

[57] ABSTRACT

A compound of formula (I)

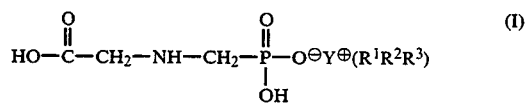

where $R^1$, $R^2$, and $R^3$ are alkyl or aralkyl or any two of $R^1$, $R^2$, and $R^3$ together form a cycloalkyl ring and Y is S or S(O) is prepared by reacting N-phosphonomethylglycine with a compound of formula (II)

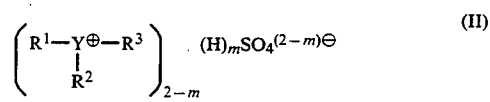

where m is 0 or 1 in the presence of a base. A preferred compound of formula (I) is trimethylsulphonium N-phosphonomethylglycine and a preferred compound of formula (II) is trimethylsulphonium hydrogen sulphate.

1 Claim, No Drawings

PROCESS FOR PREPARING SULFONIUM OR SULFOXONIUM SALTS OF N-PHOSPHONOMETHYLGLYCINE

This is a division of application Ser. No. 07/883,087, filed May 15, 1992, now U.S. Pat. No. 5,300,680.

The present invention relates to a novel process for the preparation of organic salts of N-phosphonomethylglycine.

Salts of N-phosphonomethylglycine, such as the isopropylamine and trimethyl sulphonium salts are known as active herbicides and are described for example in U.S. Pat. No. 3,799,758 and U.S. Pat. No. 4,315,765 respectively.

U.S. Pat. No 4,431,594 describes a process for the preparation of organic salts of N-phosphonomethylglycine which comprises reacting N-phosphonomethylglycine with a compound of formula $R^1R^2R^3S^+=ZX^-$ (a) wherein $R^1$, $R^2$ and $R^3$ are the same or different and are alkyl groups having from 1 to 4 carbon atoms or aromatic alkyl groups, X is chloride, bromide or iodide and Z is an electron pair or oxygen, in the presence of a trialkylamine and isolating the product by phase separation between water and a polar functional solvent which is immiscible with water. Preferred compounds of formula (a) include trimethylsulphonium chloride and preferred trialkylamines include Alamine 336 (Alamine is a trade mark of Henkel Co.).

Copending British Patent application No. 91033260.7 describes and claims trimethylsulphonium hydrogen sulphate.

The applicants have found a preferred process for obtaining organic salts of N-phosphonomethylglycine which requires simpler and less stringent reaction conditions than previous processes and which minimizes problems of plant corrosion.

According to the present invention there is provided a process for preparing a compound of formula (I) where $R^1$, $R^2$, and $R^3$ are independently selected from alkyl or aralkyl or any two of $R^1$, $R^2$, and $R^3$ together form a cycloalkyl ring and Y is S or S(O); which process comprises reacting N-phosphonomethylglycine with a compound of formula (II) where m is 0 or 1 and Y, $R^1$, $R^2$, and $R^3$ are as defined in relation to formula (I), in the presence of a base.

Preferably when $R^1$, $R^2$, or $R^3$ are alkyl or aralkyl they contain from 1–4 carbon atoms in the alkyl chain. Suitable aryl groups for inclusion in aralkyl groups $R^1$, $R^2$, or $R^3$ include phenyl.

When two of $R^1$, $R^2$, and $R^3$ are joined together to form a cycloalkyl ring, the ring suitably contains from 3 to 7 carbon atoms, preferably 6 carbon atoms.

Preferably $R^1$, $R^2$, and $R^3$ are all methyl in which case the compound of formula (I) is trimethylsulphonium N-phosphonomethylglycine.

In a preferred embodiment Y is S.

It is possible to employ in the process of the invention a mixture of a compound of formula (II) where m is 1 and an equivalent compound of formula (II) where m is 0. Preferably m is 1.

A preferred compound of formula (II) is trimethylsulphonium hydrogen sulphate of formula $(CH_3)_3S^+HSO_4^-$ as described and claimed in British Patent application No. 9103260.7.

Thus according to a further aspect of the present invention there is provided a process for preparing trimethylsulphonium N-phosphonomethylglycine, which process comprises reacting N-phosphonomethylglycine with trimethylsulphonium hydrogen sulphate in the presence of a base.

Preferably and conveniently the reaction takes place at ambient temperature and pressure.

Suitable bases for use in the reaction include amines, inorganic bases and ammonium hydroxide. Ammonium hydroxide may of course be generated by the use of ammonia gas in the aqueous phase.

Suitable amines include organic tertiary amines of formula $NR^5R^6R^7$ where $R^5$, $R^6$ and $R^7$ are independently selected from alkyl groups suitably having up to 15 carbon atoms. A particular tertiary amine base is sold under the trade name 'Alamine 336' and comprises a water insoluble symmetrical straight chain saturated tertiary amine. The alkyl groups consist of a $C_8$–$C_{10}$ mixture with the $C_8$ carbon chain predominating. This product also contains trace amounts of equivalent secondary and primary amines.

Suitable inorganic bases include for example alkali metal hydroxides such as sodium hydroxide or potassium hydroxide.

When the reaction takes place in the presence of a base which is an organic amine, such as $NR^5R^6R^7$ as hereinbefore defined, the products of the reaction (in the case when m as defined above is 1) are the compound of formula (I) and the sulphate salt of the amine $(NR^5R^6R^7H)_2SO_4$. The reaction conveniently takes place in an aqueous medium in the presence of a water-immiscible organic solvent in which the sulphate salt of the amine is soluble. The sulphate salt of the amine is thereby removed into the organic phase by phase separation and the desired product of formula (I) remains in the aqueous phase whereupon the phases may be separated. Since the compound of formula (I) is generally used in the form of an aqueous solution, it is not normally necessary to separate it from solution, although the product may if desired be concentrated by distillation, for example distillation under vacuum, to remove a proportion of the water from the aqueous phase. A suitable water-immiscible organic solvent is n-pentanol. Other water-immiscible organic solvents suitable for any given reaction conditions will readily occur to those skilled in the art.

The reaction of N-phosphonomethylglycine with the compound of formula (II) in the presence of a base may take place either in a single stage (as described above in the case of a base which is an organic amine) or in a plurality of stages.

Thus for example if the base is an alkali metal hydroxide such as sodium or potassium hydroxide or is ammonium hydroxide, an aqueous solution of the compound of formula (II) may be treated in a first stage with aqueous sodium, potassium or ammonium hydroxide and the resultant solution is reacted in a second step with N-phosphonomethyl glycine to form a compound of formula (I).

Alternatively, the N-phosphonomethylglycine and the base, for example the alkali metal hydroxide, may be reacted in a first stage and the reaction product may be subsequently reacted with the compound of formula (II) to give the product of formula (I).

When the base is an inorganic base or ammonium hydroxide, the reaction suitably takes place in an aqueous medium and in the absence of a water-immiscible organic solvent. The product of the reaction is the desired compound of formula (I) and the inorganic or ammonium sulphate or bisulphate, for example ammonium, sodium or potassium sulphate or bisulphate. The inorganic or ammonium sulphate or bisulphate may be left in solution as hereinafter described or may if desired be removed or partially remove from solution, for example by precipitation from solution.

Thus for example sodium sulphate formed by the reaction of the reaction of the compound of formula (II) with sodium hydroxide in stage (1) and the subsequent reaction of the product with N-phosphonomethylglycine in stage (2) may be removed from the aqueous reaction mixture by allowing it to crystallise as the decahydrate $Na_2SO_4.10H_2O$ and filtering it off. This may provide a convenient means of concentrating the product in the aqueous reaction solution, since part of the water will be removed with the sodium sulphate as water of crystallisation.

Similarly, the reaction conditions and concentrations in the aqueous solution may be selected such that the potassium sulphate product obtained when potassium hydroxide is used as base is precipitated from the reaction medium.

The reaction medium may optionally be cooled following completion of the reaction to reduce the solubility of the sulphate salt.

N-phosphonomethylglycine is a well known compound.

Compounds of formula (II) are suitably prepared by reacting a compound of formula (III) where $R^1$, $R^2$, and Y are as defined in relation to formula (I) with an alcohol of formula (IV) where $R^3$ is as defined in relation to formula (I); and sulphuric acid.

Compounds of formula (III) and (IV) are known compounds, or can be prepared from known compounds by conventional methods.

As indicated above, a preferred compound of formula (II) is trimethylsulphonium hydrogen sulphate of formula $(CH_3)_3S^+HSO_4^-$ as described and claimed in British Patent application No. 9103260.7.

This application describes a process for preparing trimethylsulphonium hydrogen sulphate which comprises reacting together dimethylsulphide, methanol and sulphuric acid at a temperature of from $-20°$ C. to $+100°$ C. (in a sealed system) or from $-20°$ C. to $+40°$ C. (at atmospheric pressure).

Suitably, from 1 to 10 moles of dimethylsulphide, normally about 2 moles, and from 1 to 10 moles of sulphuric acid, normally from 1 to 2 moles, are used for each mole of methanol.

In a typical preparation, the methanol is added slowly, for example dropwise, to a molar excess of dimethyl sulphide, for instance, 2 moles of dimethyl sulphide for each mole of methanol used in the reaction, at a temperature preferably below 25° C., when the reaction is carried out at atmospheric pressure. Concentrated sulphuric acid such as commercially available 98% sulphuric acid solution, may then be added gradually to the stirred mixture maintaining the temperature below 25° C. The time taken for the reaction will depend inter alia on its scale. Where half a mole of methanol (i.e. 16 g) is used, the methanol addition is completed typically in about ten minutes, and the sulphuric acid addition in about twenty minutes. Alternatively, the methanol may be added to a mixture of the sulphuric acid and dimethyl sulphide. The reaction mixture may be stirred for several hours at ambient temperature before use.

In an alternative method of preparation,, which is also described in British Patent Application No. 9103260, trimethylsulphonium hydrogen sulphate is prepared by a process which comprises reacting together dimethyl sulphide, trimethylsulphonium methyl sulphate and sulphuric acid at temperature of from $-20°$ C. to $+100°$ C. (in a sealed system) or from $-20°$ C. to $+40°$ C. (at atmospheric pressure).

This reaction is conveniently carried out by adding a molar excess of dimethyl sulphide, for example, 2 moles of dimethyl sulphide for each mole of trimethylsulphonium methyl sulphate used in the reaction, to an aqueous solution of trimethylsulphonium methyl sulphate and then adding gradually to the mixture about 2 moles of concentrated sulphuric acid, such as 98% sulphuric acid. The reaction mixture is then heated to about 40° C., when the reaction is carried out at atmospheric pressure, and stirred for several hours until reaction is complete. Trimethylsulphonium methyl sulphate is a known compound and may be prepared by the reaction of dimethyl sulphide and dimethyl sulphate.

In another method of preparation, trimethylsulphonium hydrogen sulphate is prepared by a process which comprises reacting together a trimethylsulphonium halide, sulphuric acid and hydrogen peroxide at a temperature of from 0° C. to 100° C.

This reaction is conveniently carried out by adding, with stirring, an aqueous mixture of about one mole of concentrated sulphuric acid, such as 98% sulphuric acid, and about a half mole of hydrogen peroxide, such as 30% hydrogen peroxide, to one mole of, for example, trimethylsulphonium iodide, in the presence of an inert, water immiscible, iodine-extracting solvent, such as carbon tetrachloride, in this case to remove iodine produced during the reaction. If using trimethylsulphonium chloride, the liberated chlorine can be removed using a sodium hydroxide scrubber, suitably with an inert gas flow. If using the bromide, either a bromine-extracting solvent or scrubber can be used. The trimethylsulphonium hydrogen sulphate so formed can be isolated from the aqueous phase by evaporation after the unreacted peroxide has been destroyed by the addition of, for example, palladium on carbon.

It is not necessary to isolate the compound of formula (II), for example the trimethylsulphonium hydrogen sulphate from the reaction mixture before it is employed in the process of the present invention. For example, the aqueous phase containing trimethylsulphonium hydrogen sulphate and excess sulphuric acid, if present, which is separated from the organic phase containing excess dimethyl sulphide may be used directly in the process of the present invention. The organic phase containing dimethylsulphide Ray be separated from the aqueous phase by physical phase separation or the dimethylsulphide may if desired be removed by atmospheric distillation. The latter has advantages in terms of a more convenient recovery for recycle and in ensuring that no desired product is lost by partition into the organic phase.

Thus according to a further aspect of the present invention there is provided a process for preparing trimethylsulphonium N-phosphonomethylglycine which process comprises the steps of
i) reacting together excess dimethylsulphide, methanol and sulphuric acid at a temperature of from $-20°$ C. to $+100°$ C. (in a sealed system) or from $-20°$ C. to $+40°$ C. (at atmospheric pressure) and thereafter separating the aqueous solution containing trimethylsulphonium hydrogen sulphate from the organic phase; or reacting together excess dimethylsulphide, trimethylsulphonium methyl sulphate and sulphuric acid at a temperature of from −20° C. to +100° C. (in a sealed system) or from −20° C. to +40° C. (at atmospheric pressure) and thereafter separating the aqueous solution containing trimethylsulphonium hydrogen sulphate from the organic phase; or reacting together a trimethylsulphonium halide, sulphuric acid and hydrogen peroxide at a temperature of from 0° C. to 100° C. and thereafter destroying unreacted peroxide; and subsequently ii) reacting N-phosphonomethylglycine with the aqueous solution containing trimethylsulphonium hydrogen sulphate formed in step (i) in the presence of a base.

The compound of formula (II) is preferably present in the stoichiometric proportion of 1 mole of compound of formula (II) per mole of N-phosphonomethylglycine. There is preferably used at least the stoichiometric proportion of available base per mole of N-phosphonomethylglycine. It will be appreciated that if the compound of formula (II), for example the trimethylsulphonium hydrogen sulphate, is used without isolation as described above, the aqueous starting solution may contain excess sulphuric acid. The term "available base" as used above indicates base in excess of that necessary to neutralise any such sulphuric acid present in the aqueous starting solution. The stoichiometric proportion of available base is two equivalents per mole of N-phosphonomethylglycine. There is preferably used from 2 to 3, for example from 2 to 2.5 equivalents of base per mole of N-phosphonomethylglycine.

As has been noted above, the by-product derived from the process of the present invention is the sulphate salt of the base which may be separated by the various means described. It is a particular advantage of the process of the present invention when using ammonia as base that the product ammonium sulphate can be an advantageous adjuvant in formulations of glyphosate salts.

Thus according to a further aspect of the present invention there is provided a process for the manufacture of an aqueous formulation comprising trimethylsulphonium N-phosphonomethylglycine in admixture with ammonium sulphate which comprises the steps of:

i) reacting together excess dimethylsulphide, methanol and sulphuric acid at a temperature of from −20° C. to +100° C. (in a sealed system) or from −20° C. to +40° C. (at atmospheric pressure) and thereafter separating the aqueous solution containing trimethylsulphonium hydrogen sulphate from the organic phase; or reacting together excess dimethylsulphide, trimethylsulphonium methyl sulphate and sulphuric acid at a temperature of from −20° C. to +100° C. (in a sealed system) or from −20° C. to +40° C. (at atmospheric pressure) and thereafter separating the aqueous solution containing trimethylsulphonium hydrogen sulphate from the organic phase; or reacting together a trimethylsulphonium halide, sulphuric acid and hydrogen peroxide at a temperature of from 0° C. to 100° C. and thereafter destroying unreacted peroxide; and subsequently ii) reacting N-phosphonomethylglycine with the aqueous solution containing trimethylsulphonium hydrogen sulphate formed in step (i) in the presence of ammonium hydroxide.

The proportion of ammonium sulphate present in the formulation will depend on the proportion of excess sulphuric acid derived from the manufacture of the trimethylsulphonium hydrogen sulphate. If an increased proportion of ammonium sulphate is required in the formulation, additional sulphuric acid may be added. Similarly, the concentration of the active ingredient in the formulation will be depend on the volume of water passing through from the manufacture of trimethylsulphonium hydrogen sulphate. If a more concentrated solution is required, the appropriate proportion of water may be removed from the starting solution or from the final product, for example by vacuum distillation.

It will be appreciated that the use of ammonium hydroxide as base as described above provides a process which is not only very efficient but is also highly ecologically acceptable in producing effectively no effluent for disposal.

The following Preparations and Examples illustrate the invention.

PREPARATION 1

Preparation of Trimethylsulphonium Hydrogen Sulphate

Trimethylsulphonium iodide (9.8 g, 0.048 moles) was dissolved in water (50 ml). Sulphuric acid (4.8 g at 98%, 0.048 moles) and hydrogen peroxide (2.72 g at 30%, 0.024 moles) were each diluted to 10 ml with water and added to the stirred trimethylsulphonium iodide solution. Carbon tetrachloride (150 ml) was added to extract the iodine that was produced and the mixture was stirred for 6 hours. The layers were separated. To the aqueous layer was added carbon tetrachloride (150 ml) and this was stirred overnight. The layers were separated and the aqueous layer was extracted with aliquots of carbon tetrachloride (20 ml) until no further pink colouration was visible. Palladium on carbon (3%, 0.25 g) was added to the aqueous solution to destroy any unreacted peroxide. The solution was filtered after 60 minutes, and washed with ether (2×20 ml). The water was removed under reduced pressure to produce an oily residue which was dried under vacuum at 78° C. The oil was dissolved in hot ethanol and cooled in an acetone/solid carbon dioxide bath to produce a white solid. The solid was filtered off, maintaining the temperature below 0° C. and dried under reduced pressure at 78° C. to yield a very deliquescent residue (2.7 g, 32% yield of theory). This material was dissolved in hot ethanol and allowed to cool slowly in an acetone/solid carbon dioxide bath to produce a waxy solid. The solid was filtered off, maintaining the temperature below 0° C. and dried under reduced pressure at 80° C. to yield a very deliquescent residue, melting point 20°–21° C. $C_3H_{10}S_2O_4$ (174.2): calculated C. 20.7, H 5.8, S 36.8; found C 20.7, H 5.9, S 36.6. $^1$H NMR (DMSO-$d_6$/TMS): $\delta2.91$ (s, 9H, $CH_3$-S); 7.4–7.6(s, 1H, $HSO_4$). pH=1.8–1.9 ($HSO_4^-$).

PREPARATION 2

Preparation of Trimethylsulphonium Hydrogen Sulphate

Sulphuric acid (23.7 g at 98%, 0.237 moles) was added dropwise over 60 minutes, with stirring, to dimethyl sulphide (20.0 g at 98%, 0.156 moles) while maintaining the temperature below 25° C. Methanol (5.0 g, 0.156 moles) was slowly added to the stirred mixture maintaining the temperature below 30° C. The reaction mixture was stirred for 5 hours at room temperature then held unagitated over the weekend. Two layers were present. The upper layer was excess dimethylsulphide and the lower aqueous layer contained trimethylsulphonium hydrogen sulphate and excess sulphuric acid. The lower aqueous layer was separated off for analysis by titration.

Using a non-aqueous titration system (THF/MeOH as solvent, tetrabutyl ammonium hydroxide as base), it was shown that the aqueous layer of the reaction mixture contained a mixture of sulphuric acid and hydrogen sulphate ions ($HSO_4-$).

EXAMPLE 1

Preparation of the Trimethylsulphonium Salt of N-phosphonomethylglycine

N-phosphonomethylglycine (11 g @85% strength, 0.055 moles), water (11.4 g, 0.63 moles) and trimethylsulphonium hydrogen sulphate solution prepared as described in Preparation 2 above (14.8 g of solution, 0.06 moles) were added to the reaction flask. "Alamine 336" (84.7 g, 0.22 moles) and n-pentanol (36.3 g, 0.41 moles) were added and the mixture stirred for 1½ hours. Some solid material was still visible and so water (10 g, 0.55 moles), "Alamine 336" (36.9 g, 0.094 moles) and n-pentanol (32.6 g, 0.37 moles) were added to the reaction mixture and stirred for a further 1½ hours until no more solids were visible. The layers were allowed to settle and the lower aqueous layer containing product was separated off.

The aqueous layer was added to a flask set up for distillation. The mixture was heated and some water was removed by vacuum distillation. This yielded the desired product in solution (21.8 g, 51.8% strength,) 84% yield of theory.

EXAMPLE 2

Stage 1

Preparation of Trimethylsulphonium Hydrogen Sulphate Solution

Dimethylsulphide (49.6 g, 0.8 mole) was charged to a 250 ml flask. Sulphuric acid (58.8 g, 0.6 mole) was added dropwise with stirring over 60 minutes. The reaction mixture was cooled as necessary to maintain a temperature of less than 25° C. Methanol (12.8 g, 0.4 mole) was added dropwise over 20 minutes, again maintaining the temperature below 25° C. The reaction mixture was stirred at ambient temperature for 5 hours. Two layers were formed.

The excess dimethyl sulphide was removed by atmospheric distillation to a maximum pot temperature of 43° C. (still-head temperature 38° C.).

The final solution (94.1 g) was analyzed by ion chromatography for trimethylsulphonium ion strength of 34.8%. This suggests quantitative conversion from methanol.

A proportion of this solution was used as described in Stage 2 for the preparation of trimethylsulphonium N-phosphonomethylglycine.

Stage 2

Preparation of Trimethylsulphonium N-phosphonomethylglycine Containing Ammonium Sulphate Trimethylsulphonium hydrogen sulphate solution (21.1 g @73.9% strength, 0.0896 mole), prepared as in Stage 1 was charged to a 250 ml flask and cooled in an ice/water bath. Aqueous ammonia (20.3 g @30% strength, 0.358 mole) was added dropwise with stirring over 60 minutes. The temperature of the reaction mixture was maintained at less than 25° C. The slurry was stirred at ambient temperature for 2 hours.

N-phosphonomethylglycine (13.6 g, 0.8 mole) and water (10 ml) were charged to a clean flask. The trimethylsulphonium hydroxide/ammonium sulphate slurry was added carefully over approximately 5 minutes, followed by a water wash (8 ml). The resulting solution was stirred at ambient temperature for 2 hours.

The resulting solution contained 27% trimethylsulphonium N-phosphonomethylglycine (obtained at 98.1% yield).

EXAMPLE 3

This Example further illustrates the preparation of an aqueous solution of trimethylsulphonium N-phosphonomethylglycine containing ammonium sulphate.

Dimethylsulphide (12.2 g, 0.2 mole) was charged to a 250 ml flask. Sulphuric acid (14.7 g, 0.15 mole) was added dropwise with stirring over approximately 45 minutes. The pot temperature was maintained at 20-25 degrees C. Methanol (3.0 g, 0.1 mole) was added slowly to the mixture, again maintaining the temperature at 20-25 degrees C. The reaction mixture was stirred at ambient temperature for 4.5 hours, then held without agitation overnight.

The lower aqueous layer was separated off and charged to a clean flask with water (10 ml). Ammonium hydroxide solution (22.7 g, at 30% strength, 0.4 mole) was added dropwise with stirring at 20°-25 ° C. with cooling as necessary. A slurry was formed which was stirred at ambient temperature for 2 hours.

N-phosphonomethylglycine (13.6 g, 0.08 mole) and water (18 ml) were charged to a clean flask. The trimethylsulphonium hydroxide/ammonium sulphate slurry was added carefully over approximately 5 minutes. The temperature was maintained at 25°-30 ° C. A pale green solution was formed which was stirred at ambient temperature for 3 hours.

The resultant solution contained 18.4% trimethylsulphonium N-phosphonomethylglycine (obtained at 97.6% yield).

EXAMPLE 4

This Example illustrates the preparation of trimethylsulphonium N-phosphonomethylglycine in an aqueous formulation containing an enhanced level of ammonium sulphate.

Trimethylsulphonium hydrogen sulphate solution (25.9 g, @60% strength, 0.0896 mole) and concentrated sulphuric acid (9.6 g, 0.098 mole) were charged to a 250 ml flask and diluted with water (10 ml). Ammonium hydroxide solution (32.6 g @30% strength, 0.576 mole) was added dropwise with stirring over 60 minutes. The reaction temperature was maintained at 20°-25° C. with cooling as necessary. A slurry was formed which was stirred at ambient temperature for 2 hours.

N-phosphonomethylglycine (13. g, 0.08 mole) and water (20 ml) were charged to a clean flask. The trimethylsulphonium hydroxide/ammonium sulphate slurry was added carefully over approximately 5 minutes. The temperature was maintained at 25°-30° C. Water (10.5 ml) was added to ensure that all of the slurry was transferred. A pale green solution was formed which was stirred at ambient temperature for 3 hours.

The resultant solution contained 17.2% trimethylsulphonium N-phosphonomethylglycine (obtained in 97.6% yield).

EXAMPLE 5

This Example illustrates the preparation of trimethylsulphonium N-phosphonomethylglycine using potassium hydroxide as base.

Dimethylsulphide (16.8, 0.272 mole) was charged to a 250 ml flask. Sulphuric acid (20.0 g, 0.204 mole) was added dropwise with stirring over approximately 45 minutes. The pot temperature was maintained at 20°-25° C. Methanol (4.1 g, 0.136 mole) was added slowly to the mixture, again maintaining the temperature at 20°-25° C. The reaction mixture was stirred at ambient temperature for 4.5 hours, then held without agitation overnight.

The lower aqueous layer was separated off and charged to a clean flask. Potassium hydroxide solution (101.5 g, @28.8% strength, 0.522 mole) was added dropwise with stirring over 2 hours. The reaction temperature was maintained at 20°-25° C. with cooling as necessary. A slurry was formed which was stirred at ambient temperature for 2 hours. The potassium sulphate was filtered off and washed with water (10 ml) to give an aqueous solution.

N-Phosphonomethylglycine (16.9 g, 0.1 mole) and water (22 ml) were charged to a clean flask. The aqueous solution was added carefully over approximately 5 minutes. The temperature was maintained at 25°-30° C. A pale green solution was formed which was stirred at ambient temperature for 3 hours.

The resultant solution contained 17.2% trimethylsulphonium N-phosphonomethylglycine (obtained at 98.8% yield).

EXAMPLE 6

Trimethyl sulphonium hydrogen sulphate solution (9.5 g @71.8 strength, 0.04 mole) was charged to a 250 ml flask. Potassium hydroxide solution (28.2 g at 30.8%, 0.156 mole) was added dropwise with stirring over 2 hours. The reaction temperature was maintained at 0°-10° C. with cooling as necessary. A slurry was formed which was stirred at ambient temperature for 2 hours.

N-phosphonomethylglycine (5.6 g, 0.033 mole) and water (7 ml) were charged to a clean flask. The slurry was added carefully over approximately 5 minutes. The temperature was maintained at 0°-10° C. The potassium sulphate was filtered off after stirring for 3 hours to give a pale green solution.

The resultant solution contained 14.0% trimethylsulphonium N-phosphonomethylglycine (obtained in essentially quantitative yield).

EXAMPLE 7

N-phosphonomethylglycine (8.5, 0.05 mole) and water (10 ml) were charged to a 250 ml flask. Sodium hydroxide (6.0 g, 0.15 mole) in water (10 ml) was added carefully to the flask.

Trimethylsulphonium hydrogen sulphate solution (13.3 g @71.9% strength, 0.55 mole) was added slowly to the solution. Some material remained out of solution hence a further charge of sodium hydroxide (1.9 g, 0.049 mole) was added to give a pale green solution pH 6.

On standing white crystalline material was precipitated. This was filtered off to give the product solution.

The resultant solution contained 18.2% trimethylsulphonium N-phosphonomethylglyicine (obtained in 61.6% yield).

CHEMICAL FORMULAE
(in description)

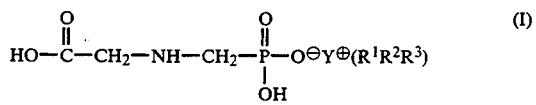

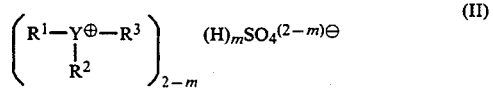

We claim:

1. A process for the manufacture of an aqueous formulation comprising trimethylsulphonium N-phosphonomethylglycine in admixture with ammonium sulphate which comprises the steps of:

i) forming trimethylsulphonium hydrogen sulphate in the presence of excess sulphuric acid by:

reacting together excess dimethylsulphide, methanol and excess sulphuric acid at a temperature of from −20° C. to +100° C. (in a sealed system) or from −20° C. to +40° C. (at atmospheric pressure) and thereafter separating the aqueous solution containing trimethylsulphonium hydrogen sulphate and excess sulphuric acid from the organic phase; or reacting together excess dimethylsulphide, trimethylsulphonium methyl sulphate and excess sulphuric acid at a temperature of from −20° C. to +100° C. (in a sealed system) or from −20° C. to +40° C. (at atmospheric pressure) and thereafter separating the aqueous solution containing trimethylsulphonium hydrogen sulphate from the organic phase; or reacting together a trimethylsulphonium halide, excess sulphuric acid and hydrogen peroxide at a temperature of from 0° C. to 100° C. and thereafter destroying unreacted peroxide; and subsequently ii) reacting the aqueous solution containing trimethylsulphonium hydrogen sulphate and excess sulphuric acid formed in step (i) with ammonium hydroxide and thereafter iii) reacting the resultant solution containing ammonium sulphate with N-phosphonomethylglycine.

* * * * *